United States Patent [19]

Mühle et al.

[11] 4,045,561

[45] Aug. 30, 1977

[54] PESTICIDAL PYRIMIDINYL PHOSPHORUS ESTERS

[75] Inventors: Herbert Mühle; Karlheinz Milzner, both of Basel; Fritz Reisser, Therwil, all of Switzerland

[73] Assignee: Sandoz Ltd., Basel, Switzerland

[21] Appl. No.: 671,446

[22] Filed: Mar. 29, 1976

Related U.S. Application Data

[63] Continuation-in-part of Ser. No. 597,473, July 21, 1975, abandoned, which is a continuation-in-part of Ser. No. 452,526, March 19, 1974, abandoned.

[30] Foreign Application Priority Data

| May 26, 1975 | Switzerland | 6724/75 |
| July 31, 1975 | Switzerland | 10002/75 |
| Jan. 6, 1976 | Switzerland | 49/76 |
| Mar. 23, 1973 | Switzerland | 4253/73 |
| Sept. 17, 1973 | Switzerland | 13328/73 |

[51] Int. Cl.$^2$ .............. C07D 239/34; C07D 239/38; A01N 9/12; A01N 9/22
[52] U.S. Cl. ................... 424/251; 260/251 P; 260/256.4 E; 260/256.5 R; 544/123
[58] Field of Search ............ 260/256 P, 256.4 E, 260/256.5 R, 247.1 B, 247.5 J; 424/251

[56] References Cited

U.S. PATENT DOCUMENTS

| 3,107,245 | 10/1963 | Gannt et al. | 260/256.4 E |
| 3,862,188 | 1/1975 | Milzner et al. | 260/256.4 E |
| 3,928,353 | 12/1975 | Milzner et al. | 260/256.4 E |
| 3,931,180 | 6/1976 | Muhle et al. | 260/256.4 E |

FOREIGN PATENT DOCUMENTS 812,656   9/1974   Belgium

Primary Examiner—Donald G. Daus
Assistant Examiner—James H. Turnipseed
Attorney, Agent, or Firm—Gerald D. Sharkin; Richard E. Vila

[57] ABSTRACT

The present invention concerns novel pyrimidinyl phosphoric and thiophosphoric esters.

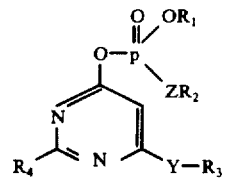

wherein
$R_1$, $R_2$ and $R_3$ are substituents, e.g. alkyl,
$R_4$ is an amino or heterocyclic function and
Z and Y are bridging functions, e.g. oxygen.
The compounds are useful insecticides.

42 Claims, No Drawings

PESTICIDAL PYRIMIDINYL PHOSPHORUS ESTERS

This is a continuation-in-part of application Ser. No. 597,473, filed July 21, 1975, which is a continuation-in-part of application Ser. No. 452,526, filed Mar. 19, 1974 now both abandoned.

The present invention relates to pyrimidinyl phosphoric and thiophosphoric esters.

The present invention provides compounds of formula I,

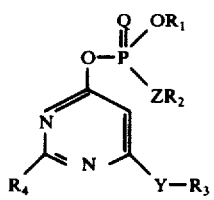

wherein $R_1$ and $R_2$, are each, independently, alkyl-($C_1$–$C_6$), $R_3$ is alkyl ($C_1$–$C_6$), cycloalkyl ($C_3$–$C_8$), phenyl, phenyl substituted by 1 to 3 members of the group chlorine, bromine and alkyl ($C_1$–$C_3$), $R_4$ is a radical —$NR_5R_6$ wherein $R_5$ and $R_6$ are each independently, hydrogen or alkyl ($C_1$–$C_6$), or $R_5$ and $R_6$ together with the nitrogen atom to which they are bound form piperidino, morpholino or pyrrolidino, or a radical –$WR_7$
wherein
W is oxygen or sulphur and
$R_7$ is alkyl ($C_1$–$C_6$)
Q and Y are each, independently, sulphur or oxygen and
Z is oxygen, sulphur or a radical

wherein $R_8$ is hydrogen or alkyl ($C_1$–$C_5$).

When any of $R_1$, $R_2$, $R_3$, $R_4$, $R_5$, $R_6$, $R_7$ and $R_8$ are or contain alkyl, this may be straight or branched chain, primary, secondary or tertiary and preferably the alkyl chain contains 1 to 4, more preferably 1 to 3, carbon atoms.

When $R_5$ and $R_6$ together with the nitrogen atom to which they are bound form a 5 or 6 membered heterocyclic ring, this is preferably a heterocyclic ring containing one or two nitrogen hetero atoms, or one nitrogen and one oxygen hetero atom, e.g. piperidino, morpholino or pyrrolidino.

The present invention further provides a process for producing the compounds of formula I which comprises reacting a compound of formula II,

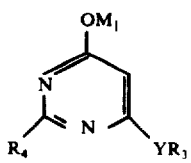

wherein $R_3$, $R_4$ and Y are as defined above and $M_1$ is hydrogen or a cation, preferably sodium or potassium, with a compound of formula III,

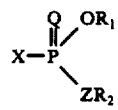

wherein $R_1$, $R_2$, Q and Z are as defined above and
X is a halogen atom, preferably chlorine.

By "halogen" as used herein is meant chlorine or bromine.

The production may be effected as follows:

To a compound of formula II, wherein $M_1$ preferably signifies sodium, in a solvent which is inert under the reaction conditions, e.g. an ester such as ethyl acetate, an amide such as dimethylformamide, an aromatic hydrocarbon such as toluene or xylene, a halogenated hydrocarbon such as chlorobenzene or chloroform, a nitrile such as acetonitrile or preferably an ether such as dioxane or tetrahydrofuran, there is added at a temperature of 0°–120° C, preferably at room temperature, and in the absence of atmospheric humidity, a compound of formula III, wherein X preferably signifies chlorine, optionally in one of the above-mentioned solvents which is inert under the reaction conditions. If in II the symbol $M_1$ signifies a hydrogen atom, the addition of an acid acceptor, such as triethyl amine or potassium carbonate, is convenient.

The reaction mixture is stirred for a period of up to approximately 20 hours, preferably at room temperature, the mixture is optionally allowed to stand for a prolonged period and then working up is effected in the usual way. The pure compounds of formula I are obtained as colourless oils or crystalline products which may be characterised, for example, by their Rf-values or melting points. They are soluble in organic solvents and may readily be emulsified with water.

The compounds of formula I, may alternatively be produced by a process which comprises reacting a compound of formula II, with a compound of formula IX,

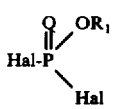

wherein
Q and $R_1$ are as defined above and
Hal is chlorine or bromine, and reacting the resulting compound with a compound of formula X,

wherein Z and $R_2$ are as defined above and
$M_4$ is hydrogen or when -$ZR_2$ is alkoxy or alkylthio, a metal cation.

When $M_1$ of formula II is hydrogen, then the compound of formula II is preferably reacted with the compound of formula IX in the presence of an acid acceptor. Preferably, however, $M_1$ is a metal cation, particularly an alkali metal cation, preferably sodium or potassium.

When $M_4$ of formula X is hydrogen, then the reaction with the compound of formula X is preferably effected in the presence of an acid acceptor.

When $-ZR_2$ of formula X is alkoxy or alkylthio, then $M_4$ is preferably a metal cation, particularly an alkali metal cation, e.g. potassium or sodium.

The above process may, for example, be carried out as follows:

A compound of formula II may be dissolved or suspended in an inert solvent or suspension medium and a compound of formula IX added thereto. The compound of formula IX may be dissolved or suspended in an inert solvent or suspension medium. Examples of inert solvents or suspension media for the compounds of formula II and IX are hydrocarbons, such as toluene or xylene, halogenated hydrocarbons, such as chloroform, nitriles such as acetonitrile, amides, such as dimethylformamide, and ethers such as tetrahydrofuran or dioxane. The addition of the compound of formula IX to the compound of formula II may be accompanied by stirring and cooling to below room temperature, e.g. to between 0° C $-80°$ C, preferably from $-5°$ C to $-70°$ C. The compounds are allowed to react for several hours, e.g. 1 or 2 hours, at a temperature between 0° and 40° C, preferably at room temperature, and even then without isolation of the resulting compound a compound of formula X is added. The addition of the compound of formula X may be accompanied by stirring and cooling to less than 0° C, e.g. $-10°$ C. The reaction mixture may be allowed to react, conveniently with stirring for up to 20 hours, e.g. 2 to 20 hours, at a temperature betwen 0° and 60° C, preferably at room temperature. Working up may be effected in conventional manner.

The reaction of a compound of formula II, wherein $M_1$ is hydrogen, with a compound of formula IX, is preferably effected in the presence of an acid acceptor, e.g. an excess of a compound of formula II or a further reagent such as an organic acid acceptor, e.g. triethylamine, or an inorganic acid acceptor, e.g. potassium carbonate.

In addition, the reaction with the compound of formula X when $M_4$ thereof is hydrogen, is preferably effected in the presence of an acid acceptor, e.g. an excess of the compound of formula X when $-ZR_2$ thereof is substituted or unsubstituted amino, or a further reagent such as an organic acid acceptor, e.g. triethylamino, or an inorganic acid acceptor, such as potassium carbonate.

The compounds of formulae IX and X are known, or may be produced in accordance with known methods.

The above described alternative process for the production of compounds of formula I, whilst the preferred mode of producing the compounds of formula I, does not form part of the present invention. Said alternative process is described and claimed in our copending application filed on even date and identified under internal code 130-3739, entitled "Improvements in or relating to organic compounds", in the name of the present inventor-applicants, the subject-matter of which application is incorporated herein by reference.

The compounds of formula II, required as starting material, may be produced as follows, viz:

Provided that $R_3$ in the compound formula II signifies an alkyl group of 1 to 6 carbon atoms or a cycloalkyl group of 3 to 8 carbon atoms and Y signifies oxygen, the production may be effected by reacting a compound of formula IV,

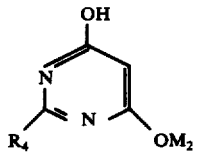

IV wherein $R_4$ is as defined above and
$M_2$ is hydrogen or a cation, preferably sodium or potassium,
with an equivalent of an alkylating reagent of formula V, $$R_9L \qquad V$$

wherein
$R_9$ is alkyl of 1 to 6 carbon atoms or cycloalkyl of 3 to 8 carbon atoms and
L is a radical $R_{10}SO_3-$,
wherein $R_{10}$ signifies a phenyl radical, or, provided that $R_3$ in the compound of formula II signifies an alkyl radical of 1 to 3 carbon atoms, by reacting the compound of formula IV, with an equivalent of dialkyl sulphate of formula VI, $$O_2S(OR_{11})_2 \qquad VI$$

wherein
$R_{11}$ is an alkyl radical of 1 to 3 carbon atoms,
under alkylation conditions in the presence of an alkali, the pH value ranging from 7.5 to 8.5, or, provided that Y in the compound II signifies sulphur, by reacting a compound of formula VII,

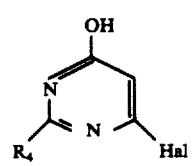

VII wherein
$R_4$ is as defined above and
Hal is chlorine or bromine, with a compound of formula VIII $$M_3SR_3 \qquad VIII$$

wherein
$R_3$ is as defined above and
$M_3$ is a cation, preferably sodium or potassium.

The compounds of formulae III, IV, V, VI, VII and VIII are known or may be produced in accordance with known processes or in analogy with processes known per se.

The compounds of formula I possess insecticidal properties and are therefore useful as insecticides. The insecticidal properties of the compounds of formula I are well illustrated in the following tests, wherein a significant insecticidal effect is observed in each test when employed at the concentrations indicated. In the tests described below, the compound of formula I is employed in the form of a liquor formulated in accordance with the emulsifiable concentrate a) described below which is diluted with water to the required concentration.

TESTS

Test 1: Insecticidal effect against Ephestia kuehniella (flour moth) - contact effect Petri dishes having a diameter of 7 cm, each containing 10 caterpillars, 10 to 12 mm in length, are sprayed by means of a spraying nozzle with 0.1 to 0.2 ml of an emulsion containing 0.05% of active agent of formula I, e.g. the compounds 0,0-Dimethyl-0-(2-diethylamino-4-ethoxy-pyrimidinyl-6)-phosphate, 0,0-Dimethyl-0-(2-dimethylamino-4-methoxy-pyrimidinyl-6)-phosphate 0,0-Dimethyl-0-(2-dimethylamino-4-ethoxy-pyrimidinyl-6)-phosphate 0,0-Dimethyl-0-(2-dimethylamino-4-methylthio-pyrimidinyl-6)-thiophosphate 0,0-Dimethyl-0-(2-diethylamino-4-methoxy-pyrimidinyl-6)thiophosphate 0,0-Diethyl-0-(2-diethylamino-4-methoxy-pyrimidinyl-6)-thiophospate 0-Methyl-0-(2-dimethylamino-4-methoxy-pyrimidinyl-6)-N-methylthiophosphoric ester amide 0-Methyl-0-(2-dimethylamino-4-ethoxy-pyrimidinyl-6)-N-methylthiophosphoric ester amide 0-Methyl-0-(2-diethylamino-4-methoxy-pyrimidinyl-6)-N-methylthiophosphoric ester amide and 0-Methyl-0-(2-diethylamino-4-ethoxy-pyrimidinyl-6)-N-methylthiophosphoric ester amide. The dishes are then covered with a fine mesh brass wire grating. After drying the coating, a wafer is given as food and renewed as required. After 5 days the rate of mortality is determined as a percentage by counting the live and dead insects. A significant effect is observed.

Test 2: Insecticidal effect against Bruchidius Obtectus (bean weevil) - contact effect Petri dishes having a diameter of 7 cm are sprayed by means of a spraying nozzle with 0.1 to 0.2 cc of an emulsion containing 0.0125% of a compound of formula I, e.g. the compounds 0,0-Dimethyl-0-(2-diethylamino-4-methoxy-pyrimidinyl-6)-thiophosphate 0,0-Diethyl-0-(2-diethylamino-4-methoxy-pyrimidinyl-6)-thiophosphate 0,0-Dimethyl-0-(2-diethylamino-4-methoxy-pyrimidinyl-6)-phosphate 0,0-Dimethyl-0-(2-diethylamino-4-ethoxy-pyrimidinyl-6)-phosphate 0,0-Dimethyl-0-(2-dimethylamino-4-methoxy-pyrimidinyl-6)-phosphate 0,0-dimethyl-0-(2-dimethylamino-4-ethoxy-pyrimidinyl-6)-phosphate 0,0-Dimethyl-pyrimidinyl-6)-thiophosphate 0-Methyl-0-(2-dimethylamino-4-methoxy-pyrimidinyl-6)-N-methyl-thiophosphoric ester amide and 0-Methyl-0-(2-dimethylamino-4-ethoxy-pyrimidinyl-6)-N-methyl-thiophosphoric ester amide After drying the coating for about 4 hours, 10 Bruchidius imagos are placed into each dish which is covered with a lid comprising a fine mesh brass wire grid. The insects are kept without food at room temperature. After 48 hours the mortality rate is determined. A significant effect is observed.

Test 3: Insecticidal effect against Prodenia litura (cotton stainer) - contact and feed effect 10 Prodenia larvae are placed into each Petri dish having a diameter of 10 cm. They are sprayed by means of a spraying nozzle with an active agent liquor of the compound of formula I, e.g. the compounds 0,0-dimethyl-0-(2-diethylamino-4-methoxy-pyrimidinyl-6)-thiophosphate and 0,0-diethyl-0-(2-diethylamino-4-methoxy-pyrimidinyl-6)-thiophosphate at a concentration of 500 ppm. Bush beans as fodder plants are treated to run off with the same liquor in accordance with the same method. The plants are allowed to dry and then given as food to the larvae in the dishes. The rate of mortality is determined after 5 days and indicated as a percentage. A significant effect is observed.

Test 4: Acaricidal effect against Tetranychus telarius (spider mite) - contact effect 20 to 30 mites (larvae and adults) are placed on each segment of bean plant leaves (Phaseolus vulgaris) which are immersed for 3 seconds in a liquor containing 0.0125% of a compound of formula I, e.g. the compounds 0,0-Dimethyl-0-(2-diethylamino-4-methoxy-pyrimidinyl-6)-thiophosphate 0,0-Diethyl-0-(2-diethylamino-4-methoxy-pyrimidinyl-6)-thiophosphate 0,0-Dimethyl-0(2-dimethylamino-4-methylthio-pyrimidinyl-6)-thiophosphate 0,0-Dimethyl-0-(2-diethylamino-4-ethoxy-pyrimidinyl-6)-phosphate 0,0-Dimethyl-0-(2-dimethylamino-4-methoxy-pyrimidinyl-6)-phosphate 0,0-Dimethyl-0-(2-dimethylamino-4-ethoxy-pyrimidinyl-6)-phosphate and 0-Methyl-0-(2-diethylamino-4-methoxy-pyrimidinyl-6)-N-methyl-thiophosphoric ester amide and then put into a dish. The dish is covered in a sloping position with a moistened filter paper in a way that slight ventilation is possible. After 48 hours the dead and live mites are counted under a binocular magnifying glass. A significant effect is observed.

Test 5: Ovicidal effect against Tetranychus telarius (spider mite) - contact effect Two days before treatment 12-15 females of Tetranychus are placed for oviposition in a ring (diameter: 2 cm) of caterpillar glue which is applied to a leaf of a bush plant. The females deposit 20 to 30 eggs over the course of 30 hours. One day before treatment the insects are removed, the leaves cut off from the plants and the peduncles put into a glass tube filled with water. The leaves of the bush bean plant with one to two days old eggs are immersed for 3 seconds in an emulsion containing 0.05% of a compound of formula I, e.g. the compound 0-methyl-0-(2-diethylamino-4-methoxy-pyrimidinyl-6)-N-methyl- thiophosphoric ester amide. The leaves are kept in a dish at room temperature over the course of 5 days. After 5 days the hatched and unhatched eggs are counted. A significant effect is observed.

Test 6: Nematocidal effect against Panagrellus redivivus (paste nematode)

1 cc of an aqueous suspension of Panagrellus redivivus, containing about 120 insects, is placed in a small cup (diameter: 5.5 cm, height: 3.2 cm) which contains 7 g of Terralite. 1 cc of an emulsion containing 0.2% of a compound of formula I, e.g. 0,0-dimethyl-0-(2-dimethylamino-4-methoxy-pyrimidinyl-6)phosphate is sprayed over the Terralite. After 48 hours the contents of the cup are examined in accordance with the extraction method of Baermann (G. Baermann: Meded. Geneesk. Lab. Weltevreden 41–47 [1971]) and the live nematodes are counted out under a binocular magnifying glass. A significant effect is observed.

It is to be understood that the term "insect", as used herein, is used in a broad sense and may include classes of animal organisms related or similar to the class Insecta, such as Nematoda and Acaridae. The terms "insecticide" and "insecticidal" as used herein should be construed accordingly.

The compounds are thus useful as insecticides particularly in animal buildings, e.g. stables, inhabited rooms, e.g. cellars and attics, and in plant loci.

For the abovementioned use, the amount of the compound to be applied will vary depending on the particular compound employed, the mode of application, ambient conditions and the effect desired. With regard to plant protection, in general an indicated amount to be applied to a plant locus between 0.01 and 5 kq/hectare.

The compounds may be employed as a composition with insecticidal carriers and diluents in solid or liquid form, e.g. spraying and dusting powders, pellets, strewing granulates, pastes, spraying liquids and aerosols.

Solid forms may include carriers such as diatomaceous earth, talc, kaolinite, attapulgite, pyrophyllite, artifical mineral fillers based on $SiO_2$ and silicates, lime, sodium sulphate decahydrate and plant material carriers, such as ground walnutshell. Adjuvants such as surfactants, including wetting and dispersing agents, e.g. sodium-lauryl sulphate, sodium dodecyl benzenesulphonate, condensation products from naphthalene sulphonate and formaldehyde, polyglycol ether and lignin derivatives such as sulphite liquor, may also be included in the case of wettable powders to be applied as a water suspension. Granulates are produced by coating or impregnating granular carrier materials such as pumice, limestone, attapulgite and kaolinite with the compounds.

Liquid forms may include non-phytotoxic diluents, such as alcohols, glycols, glycolic ethers, aliphatic and aromatic hydrocarbons, e.g. xylene, alkyl napthalenes and other petroleum distillates, and ketones, e.g. cyclohexanone and isophorone. Adjuvants, such as surface active agents, e.g. wetting and emulsifying agents, such as ployglycol ether formed by the reaction of an alkylene oxide with high molecular weight alcohols, mercaptans or alkyl phenols, and/or alkyl benzene sulphonates, may be included in emulsion concentrate forms.

Aside from the carriers, diluents and adjuvants already mentioned, adjuvants such as stabilizing agents, desactivators (for solid forms with carriers having an active surface), agents for improving adhesiveness to the surface treated, anticorrosives, defoaming agents and pigments may also be included.

Concentrate forms of composition generally contain between 1 and 90% preferably between 5 and 50% by weight of active compound.

Application forms of composition generally contain between 0.02 and 90%, preferably between 0.1 and 20% by weight of active compound.

Examples of concentrate and application forms of composition will now be described:

a. Emulsifiable concentrate (Employed in Tests 1 to 6 above 25 parts by weight of a compound of formula I are mixed with 20; parts by weight of isooctylphenyldecaglycol ether, 5 parts by weight of the calcium salt of an alkyl aryl sulphonate and 50 parts by weight of xylene, whereby a clear solution is obtained which may be readily emulsified in water. The concentrate is diluted with water to the desired concentration for use.

b. Emulsifiable concentrate 25 parts by weight of a compound of formula I are mixed with 35 parts by weight of isooctylphenyloctaglycol ether, 5 parts by weight of the calcium salt of an alkyl aryl sulphonate and 45 parts by weight of an aromatic petroleum fraction having a boiling point of 210° to 280° C ($D_{20}$ : 0.92). The concentrate is diluted with water to the desired concentration for use.

c. Spraying and dusting powder application form 25 parts by weight of a compound of formula I, 2 parts by weight of sodium-lauryl sulphate, and 3 parts by weight of sodium lignin sulphonate are mixed with 70 parts by weight of diatomaceous earth and ground until the particles have obtained a size of 10 $\mu$ as an average.

Preferred groups of compounds within the scope of formula I are the compounds of formula I, wherein i. $R_1$, $R_2$ and $R_3$, are each alkyl ($C_1$–$C_6$)
$R_4$ is dialkyl ($C_1$–$C_6$) amino
and
Q, Y and Z are each oxygen, ii. $R_1$, $R_2$ and $R_3$, are each alkyl ($C_1$–$C_6$),
$R_4$ is dialkyl ($C_1$–$C_6$) amino
Q is sulphur
and
Y and Z, are each oxygen, iii. $R_1$, $R_2$ and $R_3$, are each alkyl ($C_1$–$C_6$),
$R_4$ is dialkyl ($C_1$–$C_6$) amino,
Q and Y, are each oxygen
and
Z is —NH— iv. $R_1$, $R_2$ and $R_3$, are each alkyl ($C_1$–$C_6$),
$R_4$ is dialkyl ($C_1$–$C_6$) amino
Q and Y are each oxygen
and
Z is sulphur, v. $R_1$, $R_2$ and $R_3$, are each alkyl ($C_1$–$C_6$),
$R_4$ is alkoxy ($C_1$–$C_6$)
and
Q, Y and Z are oxygen vi. $R_1$, $R_2$ and $R_3$, are each alkyl ($C_1$–$C_6$),
$R_4$ is alkoxy ($C_1$–$C_6$),
Q and Y, are each oxygen
and
Z is —NH—
and vii. $R_1$, $R_2$ and $R_3$, are each alkyl ($C_1$–$C_6$),
$R_4$ is dialkyl ($C_1$–$C_6$) amino
Q and Z, are each oxygen
and
Y is sulphur.

Other preferred compounds are the compounds of formula I, particularly groups (i) to (vii) above and more particularly groups (i) to (vi) above, wherein $R_1$ and $R_2$ are each methyl and $R_3$ is ethyl. In particular it has been found that compounds of formula I having an 0,0-dimethyl-0-(4-ethoxy-pyrimidinyl-6)-phosphate or thiophosphate pattern of substitution are especially active.

Examples of preferred specific compounds falling within the scope of formula I are the compounds 0,0-dimethyl-0-(2-dimethylamino-4-ethoxy-pyrimidinyl-6)-thiophosphate, 0,0-dimethyl-0-(2-diethylamino-4-ethoxy-pyrimidinyl-6)-thiophosphate, 0,0-dimethyl-0-(2-dimethylamino-4-ethoxy-pyrimidinyl-6)-phosphate, 0,0-dimethyl-0-(2-diethylamino-4-ethoxy-pyrimidinyl-6)-phosphate, 0,0-dimethyl-0-(2-ethoxy-4-methoxy-pyrimidinly-6)-thiophosphate, 0,0-diethyl-0-(2-methoxy-4-ethoxy-pyrimidinyl-6)-thiophosphate, 0,0-dimethyl-0-(2,4-diethoxy-pyrimidinyl-6)-thiophosphate, 0,0-diethyl-0-(2,4-diethoxy-pyrimidinyl-6)-thiophosphate, 0,0-diethyl-0-(2-methoxy-4-ethoxy-pyrimidinyl-6)-phosphate, 0,0-diethyl-0-(2-ethoxy-4-methoxy-pyrimidinyl-6)-phosphate, 0,0-dimethyl-0-(2-n-propoxy-4-methoxy-pyrimidinyl-6)-thiophosphate, 0,0-diethyl-0-(2-ethoxy-4-methoxy-pyrimidinyl-6)-thiophosphate, 0-methyl-0-(2-ethoxy-4-methoxy-pyrimidinyl-6)-N-methyl-thiophosphoric ester amide, and 0-n-propyl-0-(2-ethoxy-4-methoxy-pyrimidinyl-6)-N-methyl-phosphoric ester amide.

Examples of the process of the invention will now be described. In the Examples all temperatures are indicated in degrees Centigrade.

EXAMPLE 1:

0,0-Dimethyl-0-(2-diethylamino-4-methoxypyrimidinyl-6)-thiophosphate

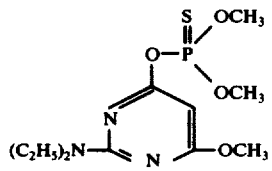

19.7 g (0.1 mol) of 2-diethylamino-4-methoxy-6-hydroxypyrimidine are added to the still hot solution of 2.4 g (1 gram-atom) of metallic sodium in 150 cc of absolute methanol. The solution is then stirred at 60° for 30 minutes, in the absence of moisture. The methanol is subsequently removed in a vacuum and the salt is dried in a high vacuum at 50° over the course of 2 hours.

The sodium salt is suspended in 150 cc of absolute tetrahydrofuran and 16.0 g (0.1 mol) of dimethyl thiophosphoric chloride are added dropwise during approx. 5 to 10 minutes, while stirring well and in the absence of air moisture. The mixture is stirred at room temperature for 16 hours. The reaction mixture together with approx. 400 cc of ether is poured into a separatory funnel, washed with water and three times with 150 cc of ice-cold sodium hydroxide solution 2N and subsequently with cold water until the last washing liquor reacts neutrally.

The organic phase is dried with sodium sulphate, treated, if desired, with animal charcoal, filtered and the solvent is removed in a vacuum. After drying in a high vacuum, the product may be purified by molecular distillation. A colourless oil, which crystallizes while standing in a refrigerator, is obtained at a temperature of 90° at $10^{-3}$mm. M.P.: 35°.

Determination of purity in accordance with thin layer chromatography may be effected on silica gel plates, using tetrahydrofuran as eluant, $R_f = 0.63$.

| Analysis: | $C_{11}H_{20}N_3O_4PS$ | Molecular weight: 321.3 | | |
|---|---|---|---|---|
| Calc. | C 41.1 % | H 6.3 % | N 13.1 % | P 9.6 % |
| Found | 41.2 % | 6.4 % | 13.0 % | 9.6 % |
| | S 10.0 % | | | |
| | 10.4 % | | | |

The reaction may also be effected by using acetic ester, dimethyl formamide, toluene, chlorobenzene, acetonitrile and dioxane as reaction media.

The following compounds of general formula I, wherein $R_4$ signifies a radical $-NR_5R_6$ and Z signifies oxygen, may be produced in analogy with the process described in Example 1.

The indicated Rf values refer to thin layer chromatography on silica gel plates with fluorescence indicator, using as eluant chloroform/acetone/methanol 25% aqueous ammonia (80:60:5:2.5).

| Exp. No. | R₁ | R₂ | R₃ | R₅ | R₆ | Y | Q | Empirical formula | Molecular weight | M.P. [°C] R$_f$ value | Analysis % Calc. / Found | | | |
|---|---|---|---|---|---|---|---|---|---|---|---|---|---|---|
| | | | | | | | | | | | C | H | N | P | S |
| 2 | C₂H₅ | C₂H₅ | C₂H₅ | CH₃ | CH₃ | O | S | C₁₂H₂₂NO₃PS | 335.3 | oil 0.73 | 43.0 / 43.8 | 6.6 / 6.6 | 12.5 / 12.3 | 9.2 / 9.5 | 9.6 / 9.8 |
| 3 | C₂H₅ | CH₃ | C₂H₅ | CH₃ | CH₃ | O | S | C₁₀H₁₈NO₃PS | 307.3 | 39–40° 0.70 | 39.1 / 38.1 | 5.9 / 6.1 | 13.7 / 13.8 | 10.1 / 10.5 | 10.4 / 10.5 |
| 4 | C₂H₅ | CH₃ | C₂H₅ | C₂H₅ | C₂H₅ | O | S | C₁₄H₂₆NO₃PS | 363.4 | oil 0.75 | 46.3 / 45.7 | 7.2 / 7.0 | 11.6 / 11.5 | 8.5 / 8.6 | 8.8 / 9.0 |
| 5 | C₂H₅ | CH₃ | C₂H₅ | CH₃ | C₂H₅ | O | S | C₁₂H₂₂NO₃PS | 335.3 | oil 0.74 | 43.0 / 42.6 | 6.6 / 6.7 | 12.5 / 12.5 | 9.2 / 9.2 | 9.6 / 9.6 |
| 6 | C₂H₅ | CH₃ | C₂H₅ | C₂H₅ | CH₃ | O | S | C₁₁H₂₀NO₃PS | 321.3 | oil 0.70 | 41.1 / 41.0 | 6.3 / 6.4 | 13.1 / 12.9 | 9.6 / 9.9 | 10.0 / 10.3 |
| 7 | C₂H₅ | CH₃ | C₂H₅ | CH₃ | CH₃ | O | S | C₉H₁₆NO₃PS | 293.3 | 33° 0.69 | 36.9 / 36.7 | 5.5 / 5.6 | 14.3 / 14.2 | 9.9 / 10.5 | 10.9 / 10.9 |
| 8 | C₂H₅ | CH₃ | C₂H₅ | CH₃ | CH₃ | O | S | C₁₃H₂₄NO₃PS | 349.4 | oil 0.64 | 44.5 / 44.7 | 6.9 / 6.9 | 12.0 / 12.0 | 8.9 / 9.0 | 9.2 / 9.3 |
| 9 | C₂H₅ | CH₃ | n-C₃H₇ | C₂H₅ | n-C₃H₇ | O | S | C₁₄H₂₆NO₃PS | 377.4 | oil 0.70 | 47.7 / 47.9 | 7.5 / 7.5 | 11.1 / 11.0 | 8.2 / 8.3 | 8.6 / 8.5 |
| 10 | CH₃ | CH₃ | n-C₃H₇ | n-C₃H₇ | n-C₃H₇ | O | S | C₁₄H₂₆NO₃PS | 347.3 | oil 0.64 | 48.4 / 48.7 | 7.7 / 7.7 | 12.1 / 12.0 | 8.9 / 8.8 | 8.5 / 8.6 |
| 11 | CH₃ | CH₃ | C₂H₅ | C₂H₅ | C₂H₅ | O | S | C₁₁H₂₀NO₃PS | 305.3 | oil 0.63* | 43.4 / 43.3 | 6.8 / 6.8 | 13.6 / 13.8 | 10.0 / 10.1 | |

| Exp. No. | R₁ | R₂ | R₃ | R₅ | R₆ | Y | Q | Empirical formula | Molecular distillation Rf-value | Analysis % Calc. / Found | | | | |
|---|---|---|---|---|---|---|---|---|---|---|---|---|---|---|
| | | | | | | | | | | C | H | N | P | S |
| 12 | CH₃ | CH₃ | C₂H₅ | C₂H₅ | C₂H₅ | O | O | C₁₂H₂₂NO₃P | 319.3 | 85°/10⁻⁴mm 0.61 | 45.1 / 44.9 | 6.9 / 7.0 | 13.2 / 13.2 | 9.7 / 9.8 | |
| 13 | CH₃ | CH₃ | C₂H₅ | C₂H₅ | CH₃ | O | O | C₉H₁₆NO₃P | 277.22 | 95°/10⁻⁴mm 0.58 | 39.0 / 39.2 | 5.8 / 6.0 | 15.2 / 14.9 | 11.2 / 10.9 | |
| 14 | CH₃ | CH₃ | C₂H₅ | CH₃ | CH₃ | O | O | C₁₀H₁₈NO₃P | 291.24 | 95°/10⁻⁴mm 0.61 | 41.2 / 41.3 | 6.2 / 6.3 | 14.4 / 14.5 | 10.6 / 10.3 | |
| 15 | CH₃ | CH₃ | C₂H₅ | CH₃ | C₂H₅ | O | O | C₁₁H₂₀NO₃P | 321.33 | 120°/10⁻³mm 0.68 | 40.5 / 41.1 | 6.0 / 6.3 | 13.1 / 13.1 | 9.3 / 9.6 | |
| 16 | CH₃ | CH₃ | C₂H₅ | CH₃ | -nC₃H₇ | O | S | C₁₃H₂₄NO₃PS | 349.39 | 120°/10⁻³mm 0.70 | 44.5 / 44.5 | 6.8 / 6.9 | 12.9 / 13.1 | 8.9 / 9.3 | 9.2 / 9.2 |
| 17 | CH₃ | CH₃ | C₂H₅ | -nC₃H₇ | -nC₃H₇ | O | S | C₁₅H₂₂NO₃PS | 333.32 | 100°/10⁻³mm 0.63 | 46.8 / 47.4 | 7.3 / 7.5 | 11.7 / 12.6 | 9.3 / 9.0 | 9.3 |
| 18 | CH₃ | CH₃ | -nC₃H₇ | -nC₃H₇ | -nC₃H₇ | O | S | C₁₅H₂₆NO₃PS | 363.4 | 110°/10⁻³mm 0.67 | 46.4 / 47.4 | 7.2 / 7.5 | 12.6 / 12.9 | 9.0 / 9.0 | |
| 19 | CH₃ | CH₃ | C₂H₅ | CH₃ | -CH₃ | O | S | C₈H₁₈NO₃PS₂ | 309.35 | 0.63 | 34.9 / 34.5 | 5.3 / 5.3 | 13.2 / 13.6 | 10.0 / 10.0 | 8.8 / 9.0 |
| 20 | CH₃ | CH₃ | -C₂H₅ | -CH₃ | -CH₃ | S | S | C₁₀H₁₈NO₃PS₂ | 323.38 | 0.67 | 37.1 / 37.5 | 5.6 / 5.9 | 13.0 / 12.5 | 9.6 / 9.7 | 20.5 / 20.7 |
| 21 | -CH₃ | -CH₃ | -nC₃H₇ | -C₂H₅ | -CH₃ | O | O | C₁₁H₂₀NO₃P | 305.27 | 0.65 | 43.3 / 44.0 | 6.6 / 6.7 | 13.8 / 13.8 | 10.1 / 9.9 | 19.8 / 19.9 |

*Thin layer, eluant: tetrahydrofuran

The following compounds of general formula I may also be produced in analogous manner to that described in Example 1:

EXAMPLE 22:

0-Methyl-0-(2-methoxy-4-ethoxy-pyrimidinyl6)-N-methyl-thiophosphoric ester amide Light coloured oil, thin layer chromatography on silica gel plates with fluorescence indicator, using ether as eluant, $R_f = 0.53$

| Analysis: | $C_9H_{16}N_3O_4PS$ | | Molecular weight: 293.3 | | |
|---|---|---|---|---|---|
| Calc. | C 36.9 % | H 5.5 % | N 14.3 % | P 10.6 % | S 10.9 |
| Found | 36.6 % | 5.6 % | 14.3 % | 10.4 % | 11.0 |

EXAMPLE 23:

0-Methyl-0-(2-methoxy-4-methoxypyrimidinyl-6)-N-methyl-thiophosphoric ester amide Light coloured oil, thin layer chromatography as described in Example 22, $R_f = 0.45$

| Analysis: | $C_8H_{14}N_3O_4PS$ | | Molecular weight: 279 | | |
|---|---|---|---|---|---|
| Calc. | C 34.4 % | H 5.1 % | N 15.0 % | P 11.1 % | S 11.5 |
| Found | 34.6 % | 5.1 % | 15.3 % | 11.4 % | 11.7 |

EXAMPLE 24

0,0-Dimethyl-0-(2-methoxy-4-methoxypyrimidinyl-6)-thiophosphate

Light coloured oil, thin layer chromatography as described in Example 22, $R_f = 0.55$

| Analysis: | $C_8H_{13}N_2O_5PS$ | | Molecular weight: 280.2 | | |
|---|---|---|---|---|---|
| Calc. | C 34.3 % | H 4.7 % | N 10.0 % | P 11.1 % | S 11.4 % |
| Found | 33.9 % | 4.6 % | 10.0 % | 10.9 % | 11.6 % |

EXAMPLE 25

0,0-Dimethyl-0-(2-methylthio-4-ethoxypyrimidinyl-6)-thiophosphate

Colourless crystals, M.P.: 36°-38° Thin layer chromatography as described in Example 22, $R_f = 0.65$

| Analysis: | $C_9H_{15}N_2O_4PS_2$ | | Molecular weight: 310.3 | | |
|---|---|---|---|---|---|
| Calc. | C 34.8 % | H 4.9 % | N 9.0 % | P 10.0 % | S 20.7 % |
| Found | 34.6 % | 5.1 % | 9.1 % | 9.7 % | 21.0 % |

EXAMPLE 26

0-Methyl-0-(2-di-n-propylamino-4-methoxypyrimidinyl-6)-N-methyl-phosphoric ester amide 11.3 g (0.05 mol) of 2-di-n-propylamino-4methoxy-6-hydroxy-pyrimidine are added to the still hot solution of 1.5 g (0.05 g atom) of sodium in 100 cc of absolute methanol. The solution is stirred at 60° over the course of 30 minutes in the absence of moisture. The methanol is subsequently removed in a vacuum and the salt is dried in a high vacuum at 50° over the course of 2 hours.

Simultaneously, 3.1 g (0.05 mol) of methylamine in 3.1 g (0.05 mol) of absolute toluence together with 5.1 g (0.05 mol) of absolute triethyl amine, which is dissolved in 25 cc of absolute toluene, are added dropwise at −10° over the course of 1 hour and with stirring, to 7.45 g (0.05 mol) of methyl phosphoric dichloride in 80 cc of absolute toluene. The mixture is subsequently stirred at room temperature for 15 minutes, the precipitated triethyl ammonium hydrochloride is filtered by suction and, if possible, without moisture. Subsequently it is washed with 10-20 cc of absolute toluene. The clear filtrate is quickly added with stirring to the above described sodium salt of the 2-di-n-propylamino-4methoxy-6-hydroxy-pyrimidine in 150 cc of absolute toluene. The reaction mixture is stirred at room temperature over the course of 16 hours, washed once with ice-cold water, then twice with sodium hydroxide solution 2N and subsequently with cold water until the last wash liquor reacts neutrally. The organic phase is dried over sodium sulphate, treated, where required, with animal charcoal, filtered and the solvent is removed in a vacuum. After drying in a high vacuum, the product may be purified by molecular distillation. A yellowish oil is obtained at a finger temperature of 120° at $10^{-3}$ mm. $R_f$-value = 0.54

| Analysis: | $C_{13}H_{25}N_4O_4P$ | | Molecular weight: 332.34 | |
|---|---|---|---|---|
| Calc. | C 47.0 % | H 7.6 % | N 16.9 % | P 9.3 % |
| Found | 47.3 % | 7.8 % | 16.9 % | 9.3 % |

The following compounds of general formula I, wherein Z signifies —NH—, may be produced in analogy with Example 1 or 26. The indicated $R_f$-values refer to thin layer chromatography on silica gel plates with fluorescence indicator, using as eluant chloroform-/acetone/methanol/ 25% aqueous ammonia (80:60:5:2.5).

EXAMPLE 27

0-Methyl-0-(2-di-n-propylamino-4-ethoxy-pyrimidinyl-6)-N-methyl-phosphoric ester amide $R_f$-value = 0.53

| Analysis: | $C_{14}H_{27}N_4O_4P$ | | Molecular weight: 346.37 | |
|---|---|---|---|---|
| Calc. | C 48.5 % | H 7.9 % | N 16.2 % | P 8.9 % |

15

-continued

| Analysis: | $C_{14}H_{27}N_4O_4P$ | | Molecular weight: 346.37 | |
|---|---|---|---|---|
| Found | 48.7 % | 8.0 % | 15.9 % | 8.7 % |

EXAMPLE 28:

0-Methyl-0-(2-dimethylamino-4-methoxy-pyrimidinyl-6)-N-methyl-phosphoric ester amide

M.P.: 85°–86°

| Analysis: | $C_9H_{17}N_4O_4P$ | | Molecular weight: 276.23 | |
|---|---|---|---|---|
| Calc. | C 39.1 % | H 6.2 % | N 20.3 % | P 11.2 % |
| Found | 39.5 % | 6.3 % | 20.2 % | 10.7 % |

EXAMPLE 29:

0-Methyl-0-(2-dimethylamino-4-ethoxy-pyrimidinyl-6)-N-methyl-phosphoric ester amide

M.P.: 69°–70.5°

| Analysis: | $C_{10}H_{19}N_4O_4P$ | | Molecular weight: 290.26 | |
|---|---|---|---|---|
| Calc. | C 41.4 % | H 6.6 % | N 19.3 % | P 10.7 % |
| Found | 42.0 % | 6.6 % | 19.1 % | 10.4 % |

EXAMPLE 30:

0-Methyl-0-(2-diethylamino-4-methoxy-pyrimidinyl-6)-N-methyl-phosphoric ester amide

M.P.: 68°–69°

| Analysis: | $C_{11}H_{21}N_4O_4P$ | | Molecular weight: 304.28 | |
|---|---|---|---|---|
| Calc. | C 43.4% | H 7.0 % | N 18.4 % | P 10.2 % |
| Found | 43.6 % | 7.2 % | 18.3 % | 10.1 % |

EXAMPLE 31:

0-Methyl-0-(2-diethylamino-4-ethoxy-pyrimidinyl-6)-N-methyl-phosphoric ester amide

M.P.: 52.5°–53°

| Analysis: | $C_{12}H_{23}N_4O_4P$ | | Molecular weight: 318.31 | |
|---|---|---|---|---|
| Calc. | C 46.8 % | H 7.5 % | N 18.2 % | P 10.0 % |
| Found | 45.3 % | 7.5 % | 17.7 % | 9.6 % |

EXAMPLE 32

0-Methyl-0-(2-diethylamino-4-methoxy-pyrimidinyl-6)-N-methyl-thiophosphoric ester amide $R_f$-value: 0.70

| Analysis: | $C_{11}H_{21}N_4O_3PS$ | | Molecular weight: 320.35 | |
|---|---|---|---|---|
| Calc. | C 41.2 % | H 6.6 % | N 17.5 % | P 9.7 % |
| Found | 40.5 % | 6.7 % | 17.3 % | 10.0 % |
| | S 10.0 % | | | |
| | 10.1 % | | | |

16

EXAMPLE 33

0-Methyl-0-(2-diethylamino-4-ethoxy-pyrimidinyl-6)-N-methyl-thiophosphoric ester amide $R_f$-value = 0.69

| Analysis: $C_{12}H_{23}N_4O_3PS$ | | Molecular weight: 334.38 | | |
|---|---|---|---|---|
| Calc. | C 43.1 % H 6.9 % | N 16.8 % | P 9.3 % | S 9.6 % |
| Found | 42.9 % 7.0 % | 16.6 % | 9.4 % | 9.8 % |

EXAMPLE 34

0-Methyl-0-(2-dimethylamino-4-methoxy-pyrimidinyl-6)-N-methyl-thiophosphoric ester amide

M.P.: 57°–58°

| Analysis: $C_9H_{17}N_4O_3PS$ | | Molecular weight: 292.3 | | |
|---|---|---|---|---|
| Calc. | C 37.0 % H 5.9 % | N 19.2 % | P 10.6 % | S 11.0 % |
| Found | 36.1 % 6.1 % | 19.0 % | 11.0 % | 11.2 % |

EXAMPLE 35

0-Methyl-0-(2-dimethylamino-4-ethoxy-pyrimidinyl-6)-N-methyl-thiophosphoric ester amide

M.P.: 76°–77°

| Analysis: $C_{10}H_{19}N_4O_3PS$ | | Molecular weight: 306.32 | | |
|---|---|---|---|---|
| Calc. | C 39.2 % H 6.3 % | N 18.3 % | P 10.1 % | S 10.5 % |
| Found | 38.8 % 6.3 % | 18.5 % | 10.2 % | 10.2 % |

EXAMPLE 36

0-Methyl-0-(2-di-n-propylamino-4-methoxy-pyrimidinyl-6)-N-methyl-thiophosphoric ester amide $R_f$-value = 0.73

| Analysis: $C_{13}H_{25}N_4O_3PS$ | | Molecular weight: 384.4 | | |
|---|---|---|---|---|
| Calc. | C 44.8 % H 7.2 % | N 16.1 % | P 8.9 % | S 9.2 % |
| Found | 44.2 % 7.3 % | 15.9 % | 8.8 % | 9.3 % |

EXAMPLE 37

0-Methyl-0-(2-di-n-propylamino-4-ethoxy-pyrimidinyl-6)-N-methyl-thiophosphoric ester amide $R_f$-value = 0.73

| Analysis: $C_{14}H_{27}N_4O_3PS$ | | Molecular weight: 362.43 | | |
|---|---|---|---|---|
| Calc. | C 46.4 % H 7.5 % | N 15.5 % | P 8.5 % | S 8.8 % |
| Found | 45.5 % 7.8 % | 15.4 % | 8.4 % | 8.7 % |

EXAMPLE 38

0-Methyl-0-(2-dimethylamino-4-n-propoxy-pyrimidinyl-6)-N-methyl-thiophosphoric ester amide $R_f$-value = 0.72

| Analysis: $C_{11}H_{21}N_4O_3PS$ | | Molecular weight: 320.35 | | |
|---|---|---|---|---|
| Calc. | C 41.2 % H 6.6 % | N 17.5 % | P 9.7 % | S 10.0 % |
| Found | 40.8 % 6.7 % | 17.3 % | 10.0 % | 10.1 % |

The starting materials of general formula II may be produced in accordance with the following Example:

EXAMPLE 39

2-Diethylamino-4-methoxy-6-hydroxy-pyrimidine 500 cc of sodium hydroxide solution 1N are added while stirring to 91.5 g (0.5 mol) of 2-diethylamino-4,6-dihydroxy-pyrimidine. The solution is stirred at 50° for a short period and then cooled to 20°. 63 g (0.5 mol) of dimethyl sulphate are added dropwise, over the course of 1 hour, to the clear solution; by further addition of sodium hydroxide solution 1N the pH value is kept between 7.5 and 8. A total of approximately 100 cc of sodium hydroxide solution 1N is further used. The mixture is stirred for a further 5 hours at room temperature and filtered off at 5° from the precipitated crystals; then it is washed with water. The crystalline product is subsequently decomposed with 1500 cc of carbon tetrachloride by means of a vibration mixer. The undissolved parts are suction filtered and the carbon tetrachloride solution is then concentrated by evaporation, whereupon crystallization commences; 200 cc of petroleum ether are then added. The mixture is suction filtered, washed with petroleum ether and dried at 80° in a high vacuum. Optionally it may be recrystallized from benzene. M.P.: 165°–166°.

| Analysis: $C_9H_{15}N_3O_2$ | | Molecular weight: 197.2 | | |
|---|---|---|---|---|
| Calc. | C 54.8 % | H 7.7 % | N 21.3 % | O 16.2 % |
| Found | 54.5 % | 7.4 % | 21.1 % | 16.3 % |

The following compounds of general formula II may be produced in analogous manner to that described in Example 39:

EXAMPLE 40

2-Dimethylamino-4-methoxy-6-hydroxy-pyrimidine

M.P.: 215°–216°

| Analysis: $C_7H_{11}N_3O_2$ | | Molecular weight: 169.2 | | |
|---|---|---|---|---|
| Calc. | C 49.7 % | H 6.6 % | N 24.8 % | O 18.9 % |
| Found | 49.7 % | 6.4 % | 24.7 % | 19.0 % |

EXAMPLE 41

2-Di-n.propylamino-4-methoxy-6-hydroxy-pyrimidine

M.P.: 116°–117°

| Analysis: $C_{11}H_{19}N_3O_2$ | | Molecular weight: 225.3 | | |
|---|---|---|---|---|
| Calc. | C 58.6 % | H 8.5 % | N 18.7 % | O 14.2 % |
| Found | 59.3 % | 8.6 % | 18.2 % | 14.4% |

EXAMPLE 42

2-Dimethylamino-4-ethoxy-6-hydroxy-pyrimidine 155.2 g(1 mol) of 2-dimethylamino-4,6-hydroxypyrimidine are added while stirring to 1000 cc of sodium hyroxide solution 1N and the mixture is heated to 50° over a short period. 70 g (1 mol) of diethyl sulphate are subsequently added dropwise, over the course of 2 hours, at 40°–45°. During the dropwise addition the pH value is kept at between 7.5 and 8.0 by further addition of sodium hydroxide solution 1N. Approximately 500 cc of sodium hydroxide solution 1N are further employed. The mixture is stirred at 40° for 6 hours, filtered off, washed with a small amount of water and dried at 90° in a high vacuum. The compound may be recrystallized from benzene. M.P. 194°–195°. Better yields may be obtained by extracting the aqueous phase with chloroform. The chloroform solution is dried with sodium sulphate and after evaporation crystals are obtained which may be recrystallized from benzene.

| Analysis: $C_8H_{13}N_3O_2$ | | Molecular weight: 183.2 | | |
|---|---|---|---|---|
| Calc. | C 52.4 % | H 7.2 % | N 22.9 % | O 17.5 % |
| Found | 52.4 % | 7.0 % | 22.9 % | 17.8 % |

The following compounds of general formula II may be produced in analogous manner to that described in Example 42.

EXAMPLE 43

2-Diethylamino-4-ethoxy-6-hydroxy-pyrimidine

M.P.: 144°–145°

| Analysis: $C_{10}H_{17}N_3O_2$ | | Molecular weight: 211.26 | | |
|---|---|---|---|---|
| Calc. | C 57.0 % | H 8.1 % | N 19.9 % | O 15.1 % |
| Found | 57.5 % | 8.2 % | 19.8 % | 15.3 % |

EXAMPLE 44

2-Di-n.propylamino-4-ethoxy-6-hydroxy-pyrimidine

M.P.: 132°–133°

| Analysis: $C_{12}H_{21}N_3O_2$ | | Molecular weight: 239.32 | | |
|---|---|---|---|---|
| Calc. | C 60.2 % | H 8.8 % | N 17.6 % | O 13.4 % |
| Found | 60.1 % | 8.6 % | 17.4 % | 13.5 % |

EXAMPLE 45

2-Methoxy-4-ethoxy-6-hydroxypyrimidine 14.2 g (0.1 mol) of 2-methoxy-4,6-dihydroxy-pyrimidine are added while stirring to 50 cc of sodium hydroxide solution 2N and the mixture is stirred for half a hour with heating to 50°. 17.0 g (0.11 mol) of diethyl sulphate are subsequently added dropwise over the course of 20 minutes and with stirring; by adding sodium hydroxide solution 2N the pH value should, if possible, be kept at between 8 and 8.2. The mixture is then stirred at 50°, sodium hydroxide solution 2N is added from time to time until the pH remains constant (approximately 3 hours). The reaction mixture is subsequently cooled to 0°, the precipitate is suction filtered and washed with a small quantity of ethanol. After drying in a high vacuum at 80°, the substance has a M.P. of 192°–194°.

| Analysis: $C_7H_{10}N_2O_3$ | | Molecular weight: 170.2 | | |
|---|---|---|---|---|
| Calc. | C 49.4 % | H 5.9 % | N 16.5 % | O 28.2 % |
| Found | 49.5 % | 5.8 % | 16.1 % | 27.9 % |

EXAMPLE 46

2-Methoxy-4-methoxy-6-hydroxypyrimidine 142 g (1 mol) of 2-methoxy-4,6-dihydroxypyrimidine are added while stirring to 500 cc of sodium hydroxide solution 2N and the mixture is stirred at 50° for 1 hour. Subsequently it is cooled to room temperature and 139 g (1.1 mol) of dimethyl sulphate are added dropwise while stirring; by the addition of sodium hydroxide solution 2N the pH value is kept at between 8.0 and 8.2. The mixture is stirred at 50° for a further 2 hours, cooled to room temperature and extracted with chloroform. After drying the chloroform phase over sodium sulphate the solvent is decanted in a vacuum. A white powder is obtained. After decomposition with ether/chloroform (1:1), the substance has a M.P. of 197°–201°.

| Analysis: $C_6H_8N_2O_3$ | | Molecular weight: 156.1 | | |
|---|---|---|---|---|
| Calc. | C 46.1 % | H 5.1 % | N 17.9 % | O 30.8 % |
| Found | 46.3 % | 5.0 % | 17.7 % | 31.0 % |

EXAMPLE 47

2-Methylthio-4-ethoxy-6-hydroxypyrimidine 31.6 g (0.2 mol) of 2-methylthio-4,6-dihydroxypyrimidine are added, while stirring well, to 100 cc of sodium hydroxide solution 2N and the mixture is stirred at 50° for half an hour. 34.0 g (0.22 mol) of diethyl sulphate are then added dropwise and with stirring, at 50°; by the addition of sodium sulphate 2N the pH value is kept at between 8 and 8.2. Towards the end of the dropwise addition a precipitate is obtained. The mixture is subsequently stirred at 50° for 1 further hour, cooled to 0° and filtered. The precipitate is washed with cold ethanol, then with ether and dried in a high vacuum at 80°. The obtained white powder has a M.P. of 185°–187°.

| Analysis: $C_7H_{10}N_2O_2S$ | | Molecular weight: 186.2 | | | |
|---|---|---|---|---|---|
| Calc. | C 45.1 % | H 5.4 % | N 15.0 % | O 17.2 % | S 17.2 % |
| Found | 44.8 % | 5.4 % | 15.0 % | 17.6 % | 17.1 % |

EXAMPLE 48

2-Methylthio-4-methoxy-6-hydroxypyrimidine 15.8 g (0.2 mol) of 2-methylthio-4,6-dihydroxypyrimidine are added while stirring well, to 100 cc of sodium hydroxide solution 2N and the mixture is stirred at 50° for half an hour. The mixture is subsequently cooled to room temperature and 13.9 g (0.11 mol) of dimethyl sulphate are added dropwise, while stirring; by the addition of sodium hydroxide solution 2N the pH value is kept at between 8 and 8.2. After the dropwise addition a precipitate is obtained. The mixture is stirred at 50° for a further 2½ hours, whereby the pH value is kept at between 8 and 8.3, then cooled to 0° and filtered. The obtained white powder has a M.P. of 193°–195°.

| Analysis: $C_6H_8N_2O_2S$ | | Molecular weight: 172.2 | | | |
|---|---|---|---|---|---|
| Calc. | C 41.9 % | H 4.7 % | N 16.3 % | O 18.6 % | S 18.6 % |
| Found | 41.7 % | 4.6 % | 16.5 % | 18.8 % | 18.4 % |

EXAMPLE 49

2-Dimethylamino-4-n-propoxy-6-hydroxy-pyrimidine 124 g (0.8 mol) of 2-dimethylamino-4,6-dihydroxypyrimidine are stirred with 800 cc of sodium hydroxide solution 1N at 60° for 1 hour. 171 g (0.8 mol) of p-toluene-sulphonic acid-n-propyl ester are added dropwise at 90° over the course of 1 hour and the pH is kept at 8–8.5 by the dropwise addition of sodium hydroxide solution 1N. The mixture is stirred at 90° for 16 hours, cooled to 5°, neutralized with glacial acetic acid and allowed to stand at room temperature for 6 hours. The precipitated crystals are subsequently filtered by suction, washed with water, dissolved in approximately 700 cc of chloroform, dried over sodium sulphate and evaporated to dryness in a vacuum. The residue is decomposed with 500 cc of petroleum ether, filtered by suction and recrystallized from benzene, washed with petroleum ether and dried at 60° in a high vacuum. M.P.: 194°–195°

| Analysis: $C_9H_{15}N_3O_2$ | | Molecular weight: 197.24 | |
|---|---|---|---|
| Calc. | C 54.8 % | H 7.7 % | N 21.3 % |
| Found | 54.5 % | 7.7 % | 21.3 % |

EXAMPLE 50

2-Dimethylamino-4-ethylthio-6-hydroxy-pyrimidine 17.4 g (0.1 mol) of 2-dimethylamino-4-chloro-6-hydroxy-pyrimidine and 21 g (0.25 mol) of sodium-thio-ethylate are dissolved in 100 cc of absolute ethanol. The clear solution is heated to 100° over the course of 3 days in a pressure vessel. After cooling the solution is evaporated to dryness in a vacuum. The residue is dissolved in 500 cc of water, treated with animal charcoal and the pH of the filtrate is adjusted to 5–6 with glacial acetic acid. The precipitated product is filtered by suction at 5°, washed with 200 cc of cold water and dried at 90° in a vacuum. M.P.: 184°–185°

| Analysis: $C_8H_{13}N_3OS$ | | Molecular weight: 199.27 | | |
|---|---|---|---|---|
| Calc. | C 48.2 % | H 6.6 % | N 21.1 % | S 16.1 % |
| Found | 48.1 % | 6.7 % | 21.2 % | 16.1 % |

The following Example may be produced in analogy with Example 50.

EXAMPLE 51

2-Dimethylamino-4-methylthio-6-hydroxy-pyrimidine

M.P.: 233°–234°

| Analysis: $C_7H_{11}N_3OS$ | | Molecular weight: 185.5 | | |
|---|---|---|---|---|
| Calc. | C 45.3 % | H 6.0 % | N 22.6 % | S 17.3 % |
| Found | 45.7 % | 6.1 % | 22.7 % | 17.1 % |

The starting materials of general formula IV, wherein $R_4$ signifies a radical —$SR_7$ and $M_2$ signifies hydrogen, may be produced in accordance with the following Example:

EXAMPLE 52

2-Methylthio-4,6-dihydroxypyrimidine

The following process is to be effected only with gas-mask and gloves.

600 g (4.15 mols) of thiobarbituric acid are dissolved in 8 l of sodium hydroxide solution 2N. 532 g (4.15 mols) of dimethyl sulphate ae then added dropwise, while stirring at room temperature, over the course of 15 minutes, whereupon the temperature rises to approximately 38°. The solution is allowed to react for 3 hours without cooling; the reaction mixture is then boiled for approximately 10 minutes, treated with animal charcoal and after cooling, the pH value is adjusted to 1 with 900 cc of concentrated hydrochloric acid. The compound recrystallizes into colourless needles while cooling with ice. Filtration is effected and the precipitate is washed with approximately 2 l of ice-cold water.

| Analysis: $C_5H_6N_2O_2S$ | | | Molecular weight: 158.2 | | |
|---|---|---|---|---|---|
| Calc. | C 38.0 % | H 3.8 % | N 17.7 % | S 20.3 % | O 20.3 % |
| Found | 38.8 % | 3.8 % | 17.6 % | 20.2 % | 20.1 % |

The following compounds of general formula I may be prepared in analogrous manner to that described in Examples 1 to 38. Many of these compounds were submitted to one or more of the Tests 1 to 6 described above, and significant effects were observed therein.

EXAMPLE 74

0,0-Diethyl-0-(2-ethoxy-4-methoxy-pyrimidinyl-6)-thiophosphate

To a suspension of 76.8 g (0.4 mol) of the sodium salt of 2-ethoxy-4-methoxy-6-hydroxypyrimidine in 400 ml of absolute toluene are added 75.6 g of diethyl thiophosphoric chloride (0.4 mol) in 100 ml of absolute toluene, and the reaction mixture is heated at 80° C for 71½ hours. After cooling to room temperature the mixture is washed with 200 ml of 1N sodium hydroxide solution followed by three 200 ml portions of water. The organic phase is then evaporated at 50° in a rotary evaporator, whereafter a yellow oil remains.

| Ex. No. | $R_1$ | $-ZR_2$ | $R_3$ | $R_4$ | Q | Y | Empirical Formula Molecular Weight | M.P. Rf-Value | Analysis % Calc. Found C | H | N | P | S |
|---|---|---|---|---|---|---|---|---|---|---|---|---|---|
| 53 | $C_2H_5$ | $-OC_2H_5$ | $C_2H_5$ | $-OCH_3$ | S | O | $C_{11}H_{19}N_2O_5PS$ 322.3 | Oil 0.2[5)] | 41.0 41.4 | 5.9 5.8 | 8.7 8.8 | 9.6 9.8 | 9.9 10.4 |
| 54 | $CH_3$ | $-OCH_3$ | $CH_3$ | $-OC_2H_5$ | S | O | $C_9H_{15}N_2O_5PS$ 294.3 | Oil 0.25[5)] | 36.7 36.7 | 5.1 5.0 | 9.5 9.5 | 10.5 10.5 | 10.9 10.7 |
| 55 | $CH_3$ | $-NHCH_3$ | $C_2H_5$ | $-OCH_3$ | O | O | $C_9H_{16}N_3O_5P$ 277.2 | 78–79° | 39.0 39.3 | 5.8 6.0 | 15.2 15.4 | 11.2 11.3 | — — |
| 56 | $CH_3$ | $-NHCH_3$ | $CH_3$ | $-SCH_3$ | O | S | $C_8H_{14}N_3O_3PS_2$ 295.3 | Oil 0.1[2)] | 32.5 33.5 | 4.8 5.2 | 14.2 14.3 | 10.5 9.7 | 21.7 21.5 |
| 57 | $C_2H_5$ | $-OC_2H_5$ | $CH_3$ | $-SCH_3$ | S | O | $C_{10}H_{17}N_2O_4PS_2$ 324.4 | Oil 0.55[5)] | 37.0 35.2 | 5.3 5.3 | 8.6 7.6 | 9.5 10.7 | 19.8 19.9 |
| 58 | $CH_3$ | $-OCH_3$ | $C_2H_5$ | $-OCH_3$ | S | O | $C_9H_{15}N_2O_5PS$ 294.3 | Oil 0.55[2)] | 36.7 37.0 | 5.1 5.5 | 9.5 9.6 | 10.5 10.5 | 10.9 10.6 |
| 59 | $CH_3$ | $-OCH_3$ | $C_2H_5$ | $-OCH_3$ | O | O | $C_9H_{15}N_2O_6P$ 278.2 | Oil 0.55[3)] | 38.9 39.7 | 5.4 5.6 | 10.1 10.3 | 11.1 10.6 | — — |
| 60 | $CH_3$ | $-OCH_3$ | $C_2H_5$ | $-OC_2H_5$ | O | O | $C_{10}H_{17}N_2O_6P$ 292.2 | Oil 0.25[2)] | 41.1 42.8 | 5.9 6.3 | 9.6 9.7 | 10.6 9.6 | — — |

| Ex. No. | $R_1$ | $R_2$ | $R_3$ | $R_4$ | Q | Y | Empirical Formula Molecular Weight | M.P. RF-Value | Analysis % Calc. Found C | H | N | P | S |
|---|---|---|---|---|---|---|---|---|---|---|---|---|---|
| 61 | $CH_3$ | $CH_3$ | $C_2H_5$ | $-OC_2H_5$ | S | O | $C_{10}H_{17}N_2O_5PS$ 308.3 | Oil 0.3[4)] | 39.0 39.3 | 5.6 5.6 | 9.1 9.1 | 10.0 10.1 | 10.4 10.4 |
| 62 | $C_2H_5$ | $C_2H_5$ | $C_2H_5$ | $-OC_2H_5$ | O | O | $C_{12}H_{21}N_2O_5P$ 304.3 | Oil 0.35[2)] | 47.4 45.7 | 7.0 6.9 | 9.2 9.2 | 10.2 9.4 | — — |
| 63 | $C_2H_5$ | $C_2H_5$ | $C_2H_5$ | $-OC_2H_5$ | S | O | $C_{12}H_{21}N_2O_4PS$ 320.3 | Oil 0.55[2)] | 45.0 43.4 | 6.6 6.7 | 8.7 8.3 | 9.7 9.3 | 10.0 10.1 |
| 64 | $C_2H_5$ | $C_2H_5$ | $C_2H_5$ | $-OCH_3$ | O | O | $C_{11}H_{19}N_2O_6P$ 306.3 | Oil 0.25[2)] | 43.1 43.3 | 6.3 6.3 | 9.1 9.3 | 10.1 9.7 | — — |
| 65 | $CH_3$ | $CH_3$ | $CH_3$ | $-OC_2H_5$ | O | O | $C_9H_{15}N_2O_6P$ 278.2 | Oil 0.2[2)] | 38.9 38.6 | 5.4 5.6 | 10.1 10.2 | 11.1 11.2 | — — |
| 66 | $C_2H_5$ | $C_2H_5$ | $CH_3$ | $-OC_2H_5$ | O | O | $C_{11}H_{19}N_2O_6P$ 306.3 | Oil 0.3[2)] | 43.1 43.1 | 6.3 6.4 | 9.1 9.3 | 10.1 9.9 | — — |
| 67 | $CH_3$ | $CH_3$ | $CH_3$ | $-OCH_3$ | O | O | $C_8H_{13}N_2O_6P$ 264.2 | 58–60 0.15[2)] | 36.4 37.1 | 5.0 5.3 | 10.6 10.7 | 11.7 11.1 | — — |
| 68 | $CH_3$ | $CH_3$ | $CH_3$ | $OnC_3H_7$ | S | O | $C_{10}H_{17}N_2O_5PS$ 308.3 | Oil 0.2[6)] | 39.0 39.0 | 5.6 5.8 | 9.1 9.2 | 10.0 9.9 | 10.4 10.2 |
| 69 | $C_2H_5$ | $C_2H_5$ | $C_2H_5$ | $-SCH_3$ | S | O | $C_{11}H_{19}N_2O_4PS_2$ 338.4 | Oil 0.5[5)] | 39.0 39.1 | 5.7 6.0 | 8.3 8.4 | 9.2 9.0 | 19.0 18.3 |
| 70 | $CH_3$ | $CH_3$ | $C_2H_5$ | $-SCH_3$ | O | O | $C_9H_{15}N_2O_5PS$ 294.3 | 40–41 0.25[2)] | 36.7 37.7 | 5.1 5.4 | 9.5 9.7 | 10.5 10.1 | 10.9 10.8 |
| 71 | $C_2H_5$ | $C_2H_5$ | $C_2H_5$ | $-SCH_3$ | O | O | $C_{11}H_{19}N_2O_5PS$ 322.3 | Oil 0.35[2)] | 41.0 41.1 | 5.9 6.1 | 8.7 9.0 | 9.6 9.3 | 9.9 9.7 |
| 72 | $CH_3$ | $CH_3$ | $C_2H_5$ | $SC_2H_5$ | S | O | $C_{10}H_{17}N_2O_4PS_2$ 323.4 | Oil 0.45[1)] | 37.0 36.2 | 5.3 5.3 | 8.6 8.0 | 9.5 10.0 | 19.8 19.5 |
| 73 | $CH_3$ | $CH_3$ | $C_2H_5$ | $SC_2H_5$ | O | O | $C_{10}H_{17}N_2O_5PS$ 308.3 | Oil 0.2[2)] | 39.0 40.6 | 5.6 5.9 | 9.1 9.4 | 10.0 9.1 | 10.4 11.0 |

Chromatography on silica gel.
Eluent:
[1)]Ether:n-Hexane = 1:1
[2)]Ether
[3)]Ethyl acetate
[4)]Ether:n-Hexane = 1:2
[5)]Ether:n-Hexane = 1:3
[6)]Ether:n-Hexane = 1:5
[In Examples 61–73, Z is O.]

Further compounds of general formula I may be produced in accordance with the following Examples 74 to 115.

The crude product is subjected to chromatography using a silica gel column (length 49 cm, diameter 7 cm) and 1:3 ether: n-hexane as the eluant, yielding a colourless oil, $R_f = 0.33$.

| Analysis: $C_{11}H_{19}N_2O_5PS$ | Molecular weight: 322.3 |
|---|---|

-continued

| Calc. | C 41.0 % | H 5.9 % | N 8.7 % | P 9.6 % | S 9.9 % |
|---|---|---|---|---|---|
| Found | 40.9 % | 6.6 % | 8.6 % | 9.4 % | 10.0 % |

In an analogous manner to that described in the above Example, the compounds of Examples 75 – 109 are produced.

| Example No. | $R_1$ | $-ZR_2$ | $R_3$ | $R_4$ | Q | Y | Empirical Formula Molecular Weight | M.P.° C Rf. Value | Analysis % Calc. Found | | | | |
|---|---|---|---|---|---|---|---|---|---|---|---|---|---|
| | | | | | | | | | C | H | N | P | S |
| 75 | $CH_3$ | $-NHC_2H_5$ | $C_2H_5$ | $OCH_3$ | S | O | $C_{10}H_{18}N_3O_4PS$ 307.3 | Oil 0.15) | 39.1 39.0 | 5.9 6.0 | 13.7 13.4 | 10.1 10.1 | 10.4 10.6 |
| 76 | $CH_3$ | $-NHnC_3H_7$ | $C_2H_5$ | $OCH_3$ | S | O | $C_{11}H_{20}N_3O_4PS$ 321.3 | Oil 0.452) | 41.1 41.4 | 6.3 6.6 | 13.1 13.0 | 9.6 9.5 | 10.1 10.1 |
| 77 | $CH_3$ | $-NH\text{-}isoC_3H_7$ | $C_2H_5$ | $OCH_3$ | S | O | $C_{11}H_{20}N_3O_4PS$ 321.3 | Oil 0.52) | 41.1 40.1 | 6.3 6.3 | 13.1 12.9 | 9.6 9.6 | 10.0 10.2 |
| 78 | $CH_3$ | $-NHCH_3$ | $C_2H_5$ | $OCH_3$ | O | O | $C_9H_{16}N_3O_5P$ 277.2 | 74–76 | 39.0 38.3 | 5.8 6.0 | 15.2 15.1 | 11.2 10.8 | — — |
| 79 | $CH_3$ | $-NHC_2H_5$ | $C_2H_5$ | $OCH_3$ | O | O | $C_{10}H_{18}N_3O_5P$ 291.2 | Oil | 41.2 42.3 | 6.2 6.6 | 14.4 13.7 | 10.6 9.8 | — — |
| 80 | $CH_3$ | $-NHnC_3H_7$ | $C_2H_5$ | $OCH_3$ | O | O | $C_{11}H_{20}N_3O_5P$ 305.3 | Oil | 43.3 44.5 | 6.6 6.8 | 13.8 14.5 | 10.1 10.0 | — — |
| 81 | $CH_3$ | $-NH\text{-}isoC_3H_7$ | $C_2H_5$ | $OCH_3$ | O | O | $C_{11}H_{20}N_3O_5P$ 305.3 | 53–56 | 43.3 42.5 | 6.6 6.8 | 13.8 12.9 | 10.1 9.6 | — — |
| 82 | $CH_3$ | $-NHCH_3$ | $C_2H_5$ | $OC_2H_5$ | O | O | $C_{10}H_{18}N_3O_5P$ 291.2 | Oil 0.253) | 41.2 41.5 | 6.2 6.5 | 14.4 13.9 | 10.6 11.2 | — — |
| 83 | $CH_3$ | $-NHCH_3$ | $C_2H_5$ | $OC_2H_5$ | S | O | $C_{10}H_{18}N_3O_4PS$ 307.3 | Oil 0.52) | 39.1 38.1 | 5.9 6.0 | 13.7 13.3 | 10.1 10.2 | 10.4 11.8 |
| 84 | $CH_3$ | $-NHC_2H_5$ | $C_2H_5$ | $OC_2H_5$ | S | O | $C_{11}H_{20}N_3O_4PS$ 321.3 | Oil 0.256) | 41.1 40.9 | 6.3 6.3 | 13.1 12.6 | 9.6 10.1 | 10.0 10.7 |
| 85 | $CH_3$ | $-NHC_2H_5$ | $C_2H_5$ | $OC_2H_5$ | O | O | $C_{11}H_{20}N_3O_5P$ 305.4 | Oil 0.232) | 43.3 43.3 | 6.6 6.8 | 13.8 13.8 | 10.1 9.6 | — — |
| 86 | $CH_3$ | $-NHnC_3H_7$ | $C_2H_5$ | $OC_2H_5$ | O | O | $C_{12}H_{22}N_3O_5P$ 319.3 | Oil 0.152) | 45.1 46.3 | 6.9 7.3 | 13.2 12.5 | 9.7 9.1 | — — |
| 87 | $CH_3$ | $-NHnC_3H_7$ | $C_2H_5$ | $OC_2H_5$ | S | O | $C_{12}H_{22}N_3O_4PS$ 335.4 | Oil 0.52) | 43.0 42.6 | 6.6 6.5 | 12.5 12.3 | 9.2 9.2 | 9.6 10.1 |
| 88 | $CH_3$ | $-NHCH_3$ | $CH_3$ | $OC_2H_5$ | S | O | $C_9H_{16}N_3O_4PS$ 293.3 | 77–79 | 36.9 36.7 | 5.5 5.5 | 14.3 14.5 | 10.6 10.4 | 10.9 11.3 |
| 89 | $CH_3$ | $-NHC_2H_5$ | $CH_3$ | $OC_2H_5$ | S | O | $C_{10}H_{18}N_3O_4PS$ 307.3 | 49–50 | 39.1 38.2 | 5.9 6.4 | 13.7 13.6 | 10.1 10.8 | 10.4 11.4 |
| 90 | $CH_3$ | $-NHCH_3$ | $CH_3$ | $OC_2H_5$ | O | O | $C_9H_{16}N_3O_5P$ 277.2 | 82–83 | 39.0 38.8 | 5.8 5.8 | 15.2 15.1 | 11.2 10.6 | — — |
| 91 | $CH_3$ | $-NHC_2H_5$ | $CH_3$ | $OC_2H_5$ | O | O | $C_{10}H_{18}N_3O_5P$ 291.2 | 40–41 | 41.2 41.5 | 6.2 6.3 | 14.4 14.6 | 10.4 9.9 | — — |
| 92 | $CH_3$ | $-NHCH_3$ | $CH_3$ | $OCH_3$ | O | O | $C_8H_{14}N_3O_5P$ 264.2 | 100–102 | 36.5 37.0 | 5.4 5.4 | 16.0 16.0 | 11.8 11.2 | — — |
| 93 | $CH_3$ | $-NHC_2H_5$ | $CH_3$ | $OCH_3$ | O | O | $C_9H_{16}N_3O_5P$ 278.2 | 64–66 | 39.0 37.8 | 5.8 6.0 | 15.2 15.0 | 11.2 10.8 | — — |
| 94 | $CH_3$ | $-NHC_2H_5$ | $CH_3$ | $OCH_3$ | S | O | $C_9H_{16}N_3O_4PS$ 293.3 | Oil 0.136) | 36.9 36.2 | 5.5 5.8 | 14.3 14.2 | 10.6 10.1 | 10.9 11.0 |
| 95 | $CH_3$ | $-NHCH_3$ | $CH_3$ | $OnC_3H_7$ | O | O | $C_{10}H_{18}N_3O_5P$ 291.2 | 63–64 | 41.2 41.5 | 6.2 6.4 | 14.4 14.2 | 10.6 10.7 | — — |
| 96 | $CH_3$ | $-NHCH_3$ | $CH_3$ | $OnC_3H_7$ | S | O | $C_{10}H_{18}N_3O_4PS$ 307.3 | 70–71 | 39.1 38.5 | 5.9 6.0 | 13.7 13.1 | 10.1 10.0 | 10.4 10.6 |
| 97 | $C_3H_7$ | $-NHCH_3$ | $CH_3$ | $OC_2H_5$ | O | O | $C_{11}H_{20}N_3O_5P$ 305.3 | 56–57 | 43.3 43.7 | 6.6 6.5 | 13.8 14.3 | 10.1 10.1 | — — |
| 98 | $C_2H_5$ | $N(C_2H_5)_2$ | $CH_3$ | $OC_2H_5$ | S | O | $C_{13}H_{24}N_3O_4PS$ 349.3 | Oil 0.752) | 44.7 44.7 | 6.9 7.2 | 12.0 12.3 | 8.9 9.3 | 9.2 9.3 |
| 99 | $CH_3$ | $-NHCH_3$ | $C_2H_5$ | $SCH_3$ | S | O | $C_9H_{16}N_3O_3PS_2$ 309.3 | Oil 0.62) | 34.9 33.4 | 5.2 5.4 | 13.6 13.8 | 10.0 9.9 | 20.7 20.5 |
| 100 | $CH_3$ | $-NHC_2H_5$ | $C_2H_5$ | $SCH_3$ | S | O | $C_{10}H_{18}N_3O_3PS_2$ 323.4 | Oil 0.562) | 37.1 37.8 | 5.6 6.0 | 13.0 14.9 | 9.6 10.1 | 19.8 19.6 |
| 101 | $CH_3$ | $-NHnC_3H_7$ | $C_2H_5$ | $SCH_3$ | S | O | $C_{11}H_{20}N_3O_3PS_2$ 337.4 | Oil 0.552) | 39.2 39.2 | 6.0 6.3 | 12.4 11.9 | 9.2 9.8 | 19.0 19.8 |
| 102 | $CH_3$ | $-NHCH_3$ | $C_2H_5$ | $SCH_3$ | O | O | $C_9H_{16}N_3O_4PS$ 293.3 | 95–97 | 36.9 36.7 | 5.5 5.9 | 14.3 14.3 | 10.6 10.8 | 10.9 11.2 |
| 103 | $CH_3$ | $-NHC_2H_5$ | $C_2H_5$ | $SCH_3$ | O | O | $C_{10}H_{18}N_3O_4PS$ 307.3 | 68–70 | 39.1 39.7 | 5.9 6.0 | 13.7 13.6 | 10.1 10.2 | 10.4 10.7 |
| 104 | $CH_3$ | $-NHnC_3H_7$ | $C_2H_5$ | $SCH_3$ | O | O | $C_{11}H_{20}N_3O_4PS$ 321.3 | Oil 0.152) | 41.1 41.8 | 6.3 6.6 | 13.1 13.0 | 9.6 9.4 | 10.0 10.4 |
| 105 | $CH_3$ | $-NHisoC_3H_7$ | $C_2H_5$ | $SCH_3$ | O | O | $C_{11}H_{20}N_3O_4PS$ 321.3 | 63–65 | 41.1 41.6 | 6.3 6.0 | 13.1 13.3 | 9.6 9.9 | 10.0 9.6 |
| 106 | $CH_3$ | $-NHisoC_3H_7$ | $C_2H_5$ | $SCH_3$ | S | O | $C_{11}H_{20}N_3O_3PS_2$ 337.4 | Oil 0.552) | 39.2 39.3 | 6.0 6.3 | 12.5 11.8 | 9.2 9.6 | 19.0 19.0 |
| 107 | $CH_3$ | $-NHCH_3$ | $C_2H_5$ | $SC_2H_5$ | S | O | $C_{10}H_{18}N_3O_3PS_2$ 322.3 | Oil 0.132) | 37.1 36.8 | 5.6 5.8 | 13.0 13.2 | 9.6 9.3 | 19.8 20.2 |
| 108 | $CH_3$ | $-NHCH_3$ | $C_2H_5$ | $SC_2H_5$ | O | O | $C_{10}H_{18}N_3O_4PS$ 307.3 | Oil 0.051) | 39.1 39.4 | 5.9 6.3 | 13.7 13.8 | 10.1 10.0 | 10.4 10.5 |
| 109 | $CH_3$ | $-NHCH_3$ | $CH_3$ | $SCH_3$ | S | S | $C_8H_{14}N_3O_2PS_3$ 311.4 | Oil 0.532) | 30.9 29.9 | 4.5 4.9 | 13.5 12.8 | 9.9 10.5 | 30.3 30.9 |

Thin layer chromatography on silica gel with the eluant:
2 = Ether
3 = Ethyl acetate
5 = Ether:n-hexane (1:3)
4 = Ether:n-hexane (1:2)
1 = Ether:n-hexane (1:1)

EXAMPLE 110

0,0-Diethyl-0-(2,4-dimethoxy-pyrimidinyl-6)-thiophosphate

To a suspension of 71.2 g (0.4 mol) of the sodium salt of b 2,4-dimethoxy-6-hydroxy-pyrimidine in 400 ml of absolute toluene are added 75.6 g of diethyl thiophosphoric chloride (0.4 mol) in 100 ml of absolute toluene and the reaction mixture is heated at 80° for 7½ hours. After cooling, the mixture is washed with 200 ml of 1 N sodium hydroxy solution followed by three 200 ml portions of water. The organic phase is evaporated in a rotary evaporator at 50°, yielding a yellow oil.

The crude product is subjected to chromatography using a silica gel column (length 49 cm, diameter 7 cm) and 1:3 ether:n-hexane as the eluant. The product is a colourless oil, Rf = 0.25.

| Analysis $C_{10}H_{17}N_2O_5PS$ | | Molecular weight : 308.3 | | |
|---|---|---|---|---|
| Calc. | C 39.0% | H 5.6% | N 9.1% | P 10.0% | S 10.4% |
| Found | 38.5% | 6.0% | 9.3% | 9.8% | 10.4% |

In an analogous manner to that described in the above Example are compounds indicated in the following Table are produced.

dried in vacuo at 80° C. A colourless powder, m.p. 146° - 148° C, is obtained as the product.

| Analysis: $C_7H_{10}N_2O_3$ | | Molecular Weight: 170.2 | | |
|---|---|---|---|---|
| Calc: | C 49.4% | H 5.9% | N 16.5% | O 28.2% |
| Found: | 49.1% | 5.9% | 16.6% | 28.4% |

In the following table the analytical data for the indicated starting materials are given, these starting materials being produced in an analogous manner to the procedure described in the above Example.

| Starting Material | Empirical formula Molecular weight | M.P.° C | C | H | Analysis % Calculated Found | O | S |
|---|---|---|---|---|---|---|---|
| | | | | | N | | |
| 2,4-Dimethylthio-6-hydroxy-pyrimidine | $C_6H_8N_2OS_2$ 204.2 | 195-198° | 38.3 38.4 | 4.3 4.4 | 14.9 14.9 | 8.5 9.0 | 34.1 33.7 |
| 2,4-Diethoxy-6-hydroxy-pyrimidine | $C_8H_{12}N_2O_3$ 184.3 | 137-139° | 52.2% 52.3 | 6.6% 6.6 | 15.2 15.1 | — — | — — |
| 2-n-Propoxy-4-methoxy-6-hydroxypyrimidine | $C_8H_{12}N_2O_3$ 184.3 | 117-119° | 52.2 52.6 | 6.6 6.8 | 15.2 15.5 | 26.1 26.6 | — — |
| 2-Ethylthio-4-ethoxy-6-hydroxypyrimidine | $C_8H_{12}N_2O_2S$ 200.3 | 120-121° | 48.0 47.6 | 6.0 6.0 | 14.0 13.7 | 16.0 16.3 | 16.0 16.3 |

What is claimed is:

1. A compound of the formula:

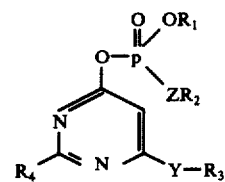

wherein $R_1$ and $R_2$, are each, independently, alkyl-($C_1$-$C_6$), $R_3$ is alkyl ($C_1$-$C_6$), cycloalkyl ($C_3$-$C_8$), phenyl phenyl

| Example No. | $R_1$ | $-ZR_2$ | $R_3$ | $R_4$ | Q | Y | Empirical Formula Molecular Weight | M.P.° C Rf. Value | Analysis Calc. Found | | | | |
|---|---|---|---|---|---|---|---|---|---|---|---|---|---|
| | | | | | | | | | C | H | N | P | S |
| 111 | $CH_3$ | $-NHnC_3H_7$ | $CH_3$ | $OC_2H_5$ | O | O | $C_{11}H_{20}N_3O_5P$ 305.3 | Oil 0.2 | 43.3 43.3 | 6.6 6.7 | 13.8 14.0 | 10.1 9.7 | — — |
| 112 | $CH_3$ | $-NH-isoC_3H_7$ | $CH_3$ | $OC_2H_5$ | O | O | $C_{11}H_{20}N_3O_5P$ 305.3 | 53-54° | 43.3 43.6 | 6.6 6.6 | 13.8 14.0 | 10.1 10.2 | — — |
| 113 | $C_2H_5$ | $-NHCH_3$ | $CH_3$ | $OC_2H_5$ | O | O | $C_{10}H_{18}N_3O_5P$ 291.2 | 58-60° | 41.2 41.1 | 6.2 6.3 | 14.4 14.3 | 10.6 10.5 | — — |
| 114 | isoC$_3$H$_7$ | $-NHCH_3$ | $CH_3$ | $OC_2H_5$ | O | O | $C_{11}H_{20}N_3O_5P$ 305.3 | 50-52° | 43.3 43.6 | 6.6 6.5 | 13.8 14.0 | 10.1 10.1 | — — |
| 115 | nC$_4$H$_9$ | $-NHCH_3$ | $CH_3$ | $OC_2H_5$ | O | O | $C_{12}H_{22}N_3O_5P$ 319.4 | 51-52° | 45.1 45.4 | 6.9 7.1 | 13.2 13.4 | 9.7 9.7 | — — |

The starting materials of general formula II may be produced in accordance with the following Examples or the Examples 39 to 52 given above.

EXAMPLE 116

2-Ethoxy-4-methoxy-6-hydroxypyrimidine

To a solution of 156 g (1.0 mol) of 2-ethoxy-4,6-dihydroxypyrimidine in 1000 ml of IN sodium hydroxide solution are added 139 g (1.1 mols) of dimethyl sulphate during a period of 15 minutes. By adding 1N sodium hydroxide solution periodically the pH value of the reaction mixture is maintained at about 7.5, using a pH meter to check the value. Once the pH value has remained constant, the reaction mixture is stirred for a further hour. The precipitate is then collected by filtration, washed twice with 250 ml of water and finally substituted by 1 to 3 members of the group chlorine, bromine and alkyl ($C_1$-$C_3$), $R_4$ is a radical -$NR_5R_6$ wherein $R_5$ and $R_6$ are each independently, hydrogen or alkyl ($C_1$-$C_6$), or $R_5$ and $R_6$ together with the nitrogen atom to which they are bound form piperdino, morpholino or pyrrolidino, or a radical $-WR_7$ wherein W is oxygen or sulphur and $R_7$ is alkyl ($C_1$-$C_6$)

Q and Y are each, independently, sulphur or oxygen and

Z is oxygen, sulphur or a radical

wherein $R_8$ is hydrogen or alkyl ($C_1$–$C_5$).

2. A compound of claim 1, wherein $R_1$, $R_2$ and $R_3$, are each alkyl ($C_1$–$C_6$), $R_4$ is dialkyl ($C_1$–$C_6$) amino and Q, Y and Z are each oxygen.

3. A compound of claim 1, wherein $R_1$, $R_2$ and $R_3$, are each alkyl ($C_1$–$C_6$), $R_4$ is dialkyl ($C_1$–$C_6$) amino, Q is sulphur and Y and Z, are each oxygen.

4. A compound of claim 1, wherein $R_1$, $R_2$ and $R_3$, are each alkyl ($C_1$–$C_6$), $R_4$ is dialkyl ($C_1$–$C_6$) amino, Q and Y are each are oxygen and Z is -NH-.

5. A compound of claim 1, wherein $R_1$, $R_2$ and $R_3$, are each alkyl ($C_1$–$C_6$), $R_4$ is dialkyl ($C_1$–$C_6$) amino, Q and Y are each oxygen and Z is sulphur.

6. A compound of claim 1, wherein $R_1$, $R_2$, and $R_3$, are each alkyl ($C_1$–$C_6$), $R_4$ is alkoxy ($C_1$–$C_6$) and Q, Y and Z are oxygen.

7. A compound of claim 1, wherein $R_1$, $R_2$ and $R_3$, are each alkyl ($C_1$–$C_6$), $R_4$ is alkoxy ($C_1$–$C_6$), Q and Y are each oxygen and Z is -NH-.

8. A compound of claim 1, wherein $R_1$ and $R_2$, are each methyl and $R_3$ is ethyl.

9. A compound of claim 1, wherein $R_1$ and $R_2$ are each methyl and Y is oxygen and $R_3$ is ethyl.

10. The compound of claim 1, which is 0,0-dimethyl-0-(2-diethylamino-4-methoxy-pyrimidinyl-6)-thiophosphate.

11. The compound of claim 1, which is 0,0-diethyl-0-(2-dimethylamino-4-ethoxy-pyrimidinyl-6)-thiophosphate.

12. The compound of claim 1, which is 0,0-dimethyl-0-(2-dimethylamino-4-ethoxy-pyrimidinyl-6)-thiophosphate.

13. The compound of claim 1, which is 0,0-diethyl-0(2-diethylamino-4-ethoxy-pyrimidinyl-6)-thiophosphate.

14. The compound of claim 1, which is 0,0-dimethyl-0-(2-dimethylamino-b 4-methoxy-pyrimidinyl-6)-thiophosphate.

15. The compound of claim 1, which is 0,0-diethyl-1-(2-diethylamino-4-methoxy-pyrimidinyl-6)-thiophosphate.

16. The compound of claim 1, which is 0,0-dimethyl-0-(2-diethylamino-4-ethoxy-pyrimidinyl-6)-thiophosphate.

17. The compound of claim 1, which is 0,0-dimethyl-0-(2-dimethylamino-4-n-propoxy-pyrimidinyl-6)-phosphate.

18. The compound of claim 1, which is 0,0-dimethyl-0-(2-di-n-propylamino-4-methoxy-pyrimidinyl-6)-phosphate.

19. The compound of claim 1, which is 0,0-dimethyl-0-(2-di-n-propoylamino-4-ethoxy-pyrimidinyl-6)-phosphate.

20. The compound of claim 1, which is 0,0-dimethyl-0-(2-diethylamino-4-methoxy-pyrimidinyl-6)-phosphate.

21. The compound of claim 1, which is 0,0-dimethyl-0-(2-dimethylamino-4-ethoxy-pyrimidinyl-6)-phosphate.

22. The compound of claim 1, which is 0,0-dimethyl-0-(2-diethylamino-4-ethoxy-pyrimidinyl-6)-phosphate.

23. The compound of claim 1, which is 0,0-dimethyl-0-(2-dimethylamino-4-methoxy-pyrimidinyl-6)-phosphate.

24. The compound of claim 1, which is 0,0-dimethyl-0-(2-dmethylamino-4-methylthio-pyrimidinyl-6)-thiophosphate.

25. The compound of claim 1, which is 0-methyl-0-(2-dimethylamino-4-methoxy-pyrimidinyl-6)-N-methylphorphoric ester amide.

26. The compound of claim 1, which is 0-methyl-0-(2-dimethylamino-4-ethoxy-pyrimidinyl-6)-N-methylphosphoric ester amide.

27. The compound of claim 1, which is 0-methyl-0(2-diethylamino-4-methoxy-pyrmidinyl-6)-methyl-phosphoric ester amide.

28. The compound of claim 1, which is 0-methyl-0-(2-diethylamino-4-ethoxy-pyrimidinyl-6)-N-methyl phosphoric ester amide.

29. The compound of claim 1, which is 0-methyl-0-(2-diethylamino-4-methoxy-pyrimidinyl-6)-N-methyl-thionophosphoric ester amide.

30. An insecticidal composition comprising an insecticidally effective amount of a compound of claim 1, in association with an insecticide carrier or diluent.

31. The insecticidal composition of claim 30, incorporating a surfactant.

32. A method of combating insects in a locus which comprises applying to the locus an insecticidally effective amount of a compound of claim 1.

33. The compound of claim 1, which is 0,0-diethyl-0-(2-methoxy-4-ethoxy-pyrimidinyl-6)-thiophosphate.

34. The compound of claim 1, which is 0,0-dimethyl-0-(2-ethoxy-4-methoxy-pyrimidinyl-6)-thiophosphate.

35. The compound of claim 1, which is 0,0-dimethyl-0-(2,4-diethoxy-pyrimidinyl-6)-thiophosphate.

36. The compound of claim 1, which is 0,0-diethyl-0-(2,4-diethoxy-pyrimidinyl-6)-thiophosphate.

37. The compound of claim 1, which is 0,0-diethyl-0-(2-methoxy-4-ethoxy-pyrimidinyl-6)-phosphate.

38. The compound of claim 1, which is 0,0-diethyl0-(2-ethoxy-4-methoxy-pyrimidinyl-6)-phosphate.

39. The compound of claim 1, which is 0,0-dimethyl-0-(2-n-propoxy-4-methoxy-pyrimidinyl-6)-thiophosphate.

40. The method of claim 32 in which the compound is 0,0-dimethyl-0-(2-ethoxy-4-methoxy-pyrimidinyl-6)thiophosphate.

41. The method of claim 32 in which the compound is 0,0-diethyl-0-(2-methoxy-4-ethoxy-pyrimidinyl-6)-thiophosphate.

42. The method of claim 32 in which the compound is 0,0-dimethyl-0-(2,4-diethoxy-pyrimidinyl-6)-thiophosphate.

* * * * *